US00PP21032P2

(12) United States Plant Patent
Burton

(10) Patent No.: US PP21,032 P2
(45) Date of Patent: Jun. 1, 2010

(54) ***COPROSMA* PLANT NAMED 'PINA COLADA'**

(50) Latin Name: *Coprosma hybrid*
Varietal Denomination: Pina Colada

(76) Inventor: Stephen Burton, 249 Peake Road, RDI Cambridge (NZ)

( * ) Notice: Subject to any disclaimer, the term of this patent is extended or adjusted under 35 U.S.C. 154(b) by 0 days.

(21) Appl. No.: 12/322,732

(22) Filed: Feb. 6, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Susan B McCormick Ewoldt
(74) *Attorney, Agent, or Firm*—Penny J. Aguirre

(57) ABSTRACT

A new cultivar of *Coprosma,* 'Pina Colada', characterized by its wavy, glossy yellow-gold leaves that intensify in winter to orange-red, its deep red-orange margins, and a compact growth habit with short branch internodes.

2 Drawing Sheets

Botanical classification: *Coprosma* hybrid.
Cultivar designation: 'Pina Colada'.

BACKGROUND OF THE INVENTION

The present invention relates to a new and distinct cultivar of *Coprosma,* botanically of hybrid origin and known as *Coprosma* 'Pina Colada' and will be referred to hereafter by its cultivar name, 'Pina Colada'. 'Pina Colada' is grown for use as a container plant and as a landscape shrub.

The new cultivar was discovered by the Inventor as a naturally occurring branch mutation of *Coprosma* cultivar 'Tequila Sunrise' (U.S. Plant Pat. No. 18,392) in a container in his nursery in the summer of 2006 in Cambridge, New Zealand.

Asexual reproduction of the new cultivar was first accomplished by the Inventor using terminal stem cuttings in Cambridge, New Zealand, in the summer of 2006. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Pina Colada' as a new and distinct cultivar of *Coprosma.*

1. 'Pina Colada' exhibits wavy, glossy leaves that are a distinct yellow-gold color with deep red-orange margins. The leaf color intensifies in the winter with more red tones.
2. 'Pina Colada' exhibits a compact growth habit with short branch internodes.

'Pina Colada' can be most closely compared to 'Tequila Sunrise', the parent plant. 'Tequila Sunrise' differs from 'Pina Colada' in having leaves that are predominately yellow-green in color with margins that are red-orange in color. In addition, the plant habit of 'Pina Colada' is more compact with shorter branch internodes than 'Tequila Sunrise'. 'Pina Colada' can also be compared to 'Yuanne' (not patented), the parent plant of 'Tequila Sunrise' and 'Evening Glow' (not patented). 'Yanne' differs from 'Pina Colada' in having leaves that are more green in color and intensify to a dark brown in winter and in having leaves that are larger than those of 'Pina Colada'. 'Evening Glow' differs from 'Pina Colada' in having leaves that are more green in color and that are flat in aspect rather than wavy.

BRIEF DESCRIPTION OF THE DRAWING

The accompanying colored photographs illustrate the overall appearance and distinct characteristics of the new *Coprosma.* The photographs were taken of a plant approximately twelve months in age as grown outdoors in a 20 cm container in Cambridge, New Zealand.

The photograph in FIG. 1 provides a an overall view of the plant habit of 'Pina Colada' and the photograph in FIG. 2 provides a close-up view of the foliage of 'Pina Colada'.

Figure 1:
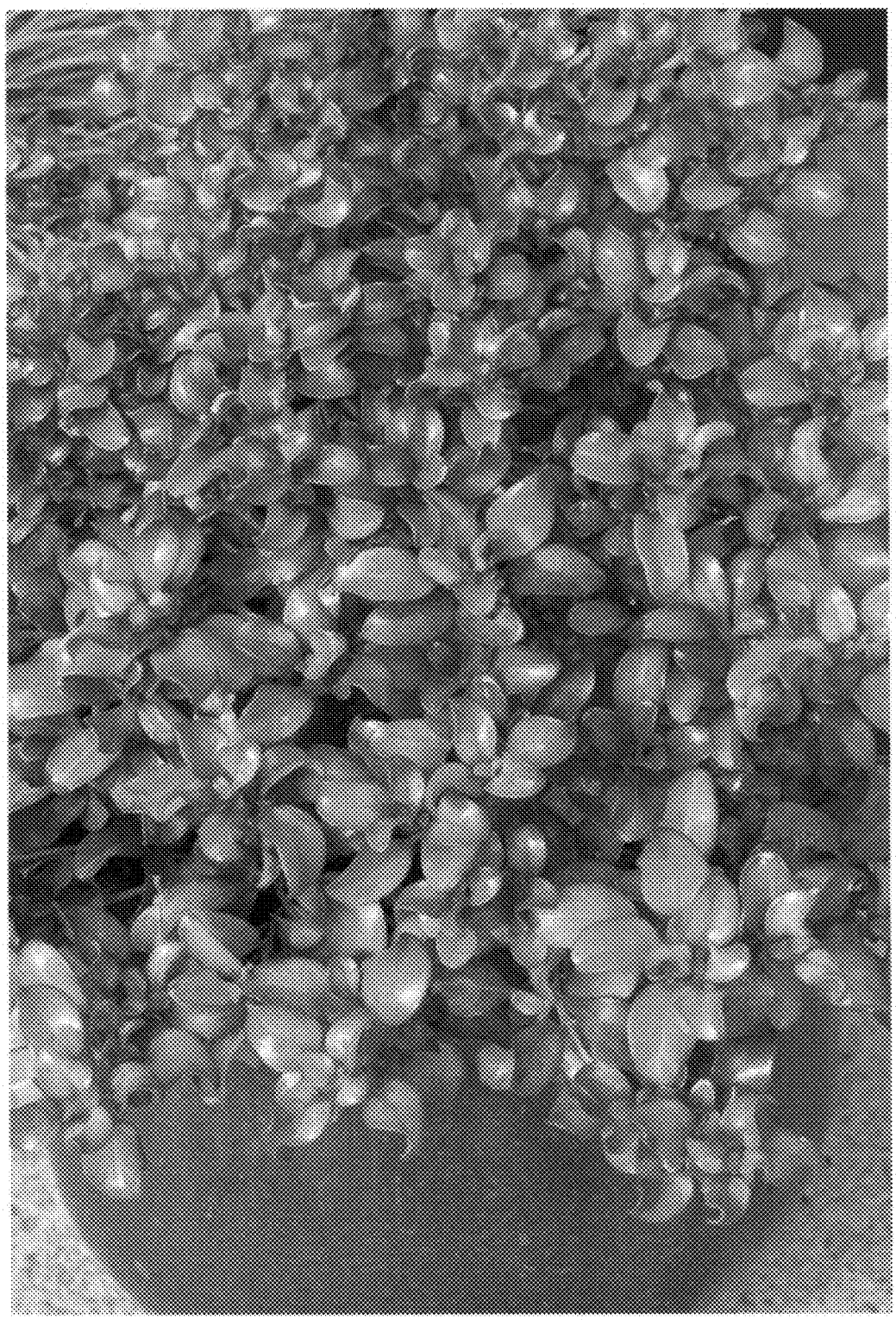
Figure 2:
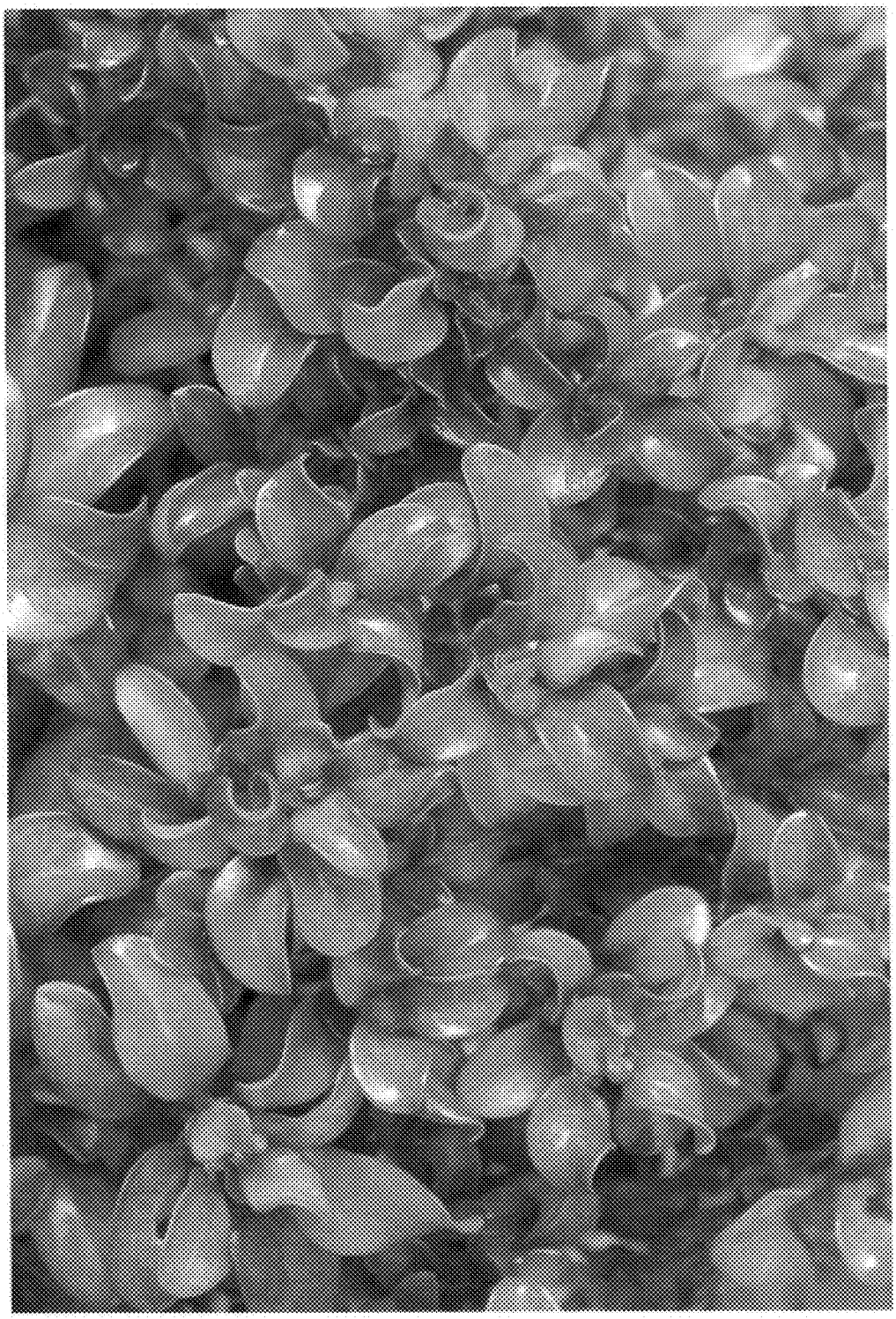

The colors in the photographs may differ slightly from the color values cited in the detailed botanical description, which accurately describe the colors of the new *Coprosma.*

DETAILED BOTANICAL DESCRIPTION OF THE PLANT

The following is a detailed description of twelve month old plants of the new cultivar as grown outdoors in 20 cm containers in Cambridge, New Zealand. Plants were grown under average day temperatures of 18° to 24° C. and average night temperatures of 4° to 10° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General plant characteristics:

*Plant type.*—Perennial shrub.
*Plant habit.*—Upright, rounded, and compact.
*Flowering period.*—No flowers observed.
*Height and spread.*—Reaches about 0.75 m in height and 0.6 m in width in a 20 cm container in 12 months.
*Hardiness.*—Tolerates temperatures at least from −3° C. to 35° C. and is cold hardy to at least U.S.D.A. Zones 9b to 10b.

*Disease resistance.*—No particular resistance to diseases has been observed.

*Root description.*—Fibrous and fine, about 2 to 3 mm in diameter, 13C in color.

Propagation and growth:

*Growth rate.*—Moderate.

*Propagation.*—Terminal stem cuttings.

*Root initiation.*—Roots appear in about 4 to 6 weeks at 20° C. under mist propagation in greenhouse conditions using natural light.

*Root development.*—Takes about 15 weeks from rooted cutting to a liner, liners take an additional 25 weeks to finishing in a 20 cm container, minimal pinching required.

Stem description:

*Stem size.*—Lateral branches range from 20 to 40 cm in length and 2 to 5 mm in width.

*Stem shape.*—Round.

*Stem color.*—152D and lightly mottled with N34A.

*Stem surface.*—Smooth, glabrous.

*Internode length.*—Average of 1.2 cm.

*Branching habit.*—Freely branched from base, average of 15 to 20 lateral branches.

*Branching aspect.*—Upright.

Foliage description:

*Leaf shape.*—Rounded to obovate.

*Leaf division.*—Simple.

*Leaf base.*—Tapered to petiole.

*Leaf apex.*—Rounded, obtuse.

*Leaf venation.*—Pinnate.

*Leaf margins.*—Entire, unevenly recurved; wavy.

*Leaf attachment.*—Petiolate.

*Leaf arrangement.*—Opposite.

*Leaf surface.*—Glabrous, glossy.

*Leaf color.*—Upper surface immature foliage; 1A surrounded by a mottling of 35A, margins N34B, lower surface immature foliage; 152D, mature foliage upper surface; 5C to 5A surrounded by a mottling of 35A, margins N34B, lower surface mature foliage 169B, winter color upper and lower surface; same as mature coloration with a greater degree of mottling of N34B on upper surface.

*Leaf number.*—Average of 30 to 40 (15 to 20 pairs) per lateral branch.

*Leaf size.*—Average of 3 to 4 cm in length and 1.5 to 2 cm in width.

*Leaf aspect.*—Wavy, slightly concave, and held at about a 45° angle to lateral branch.

*Leaf fragrance.*—None.

*Leaf venation.*—Pinnate, 168B in color on upper and lower surface.

*Leaf petiole.*—Average of 1 cm in length and 1.3 mm in width, color is 15D mottled with N34A, surface is glabrous.

Flower description: No flowers or seed production have been observed.

It is claimed:

1. A new and distinct cultivar of *Coprosma* plant named 'Pina Colada' as herein illustrated and described.

* * * * *